US012678614B2

(12) United States Patent
Peters et al.

(10) Patent No.: US 12,678,614 B2
(45) Date of Patent: Jul. 14, 2026

(54) IMPLANTABLE BLOOD PUMP FOR ASSISTING A HEART FUNCTION

(71) Applicant: Berlin Heart GmbH, Berlin (DE)

(72) Inventors: Oliver Peters, Berlin (DE); Adrian Wisniewski, Berlin (DE); Hendryk Richert, Berlin (DE)

(73) Assignee: Berlin Heart Gmbh, Berlin (DE)

( * ) Notice: Subject to any disclaimer, the term of this patent is extended or adjusted under 35 U.S.C. 154(b) by 601 days.

(21) Appl. No.: 17/434,281

(22) PCT Filed: Feb. 25, 2020

(86) PCT No.: PCT/EP2020/054949

§ 371 (c)(1),
(2) Date: Aug. 26, 2021

(87) PCT Pub. No.: WO2020/173966

PCT Pub. Date: Sep. 3, 2020

(65) Prior Publication Data

US 2022/0134084 A1 May 5, 2022

(30) Foreign Application Priority Data

Feb. 26, 2019 (EP) ..................................... 19159286

(51) Int. Cl.
*A61M 60/422* (2021.01)
*A61M 60/178* (2021.01)
(Continued)

(52) U.S. Cl.
CPC ........ *A61M 60/422* (2021.01); *A61M 60/178* (2021.01); *A61M 60/216* (2021.01);
(Continued)

(58) Field of Classification Search
CPC .............. A61M 60/422; A61M 60/178; A61M 60/216; A61M 60/237; A61M 60/242;
(Continued)

(56) References Cited

U.S. PATENT DOCUMENTS 4,065,264 A * 12/1977 Lewin ...................... A61M 1/32
165/184
5,707,218 A 1/1998 Maher et al.
(Continued)

FOREIGN PATENT DOCUMENTS

EP 3181163 A1 6/2017
EP 3590559 A1 * 1/2020 ............. H05B 1/025
(Continued)

OTHER PUBLICATIONS

Heco Inc, "How Does an Induction Electric Motor's Rotor Work?," Jul. 28, 2016. https://hecoinc.com/how-does-an-induction-electric-motors-rotor-work/ (Year: 2016).*
(Continued)

*Primary Examiner* — Amanda L Steinberg
*Assistant Examiner* — Laura Hodge
(74) *Attorney, Agent, or Firm* — Crowell & Moring LLP

(57) ABSTRACT

The present application relates to an implantable blood pump for assisting a heart function. The blood pump comprises a heat source and a wall that delimits a flow cannel. In addition, the blood pump comprises a heat distributor for distributing heat generated by the heat source to a surface of the wall. In order to transfer heat from the heat source to the blood conveyed in the flow channel, the heat distributor is thermally conductively connected to the heat source and thermally conductively connected to the opposite face of the wall from the flow channel.

20 Claims, 5 Drawing Sheets

(51) Int. Cl.

| | |
|---|---|
| *A61M 60/216* | (2021.01) |
| *A61M 60/237* | (2021.01) |
| *A61M 60/242* | (2021.01) |
| *A61M 60/508* | (2021.01) |
| *A61M 60/814* | (2021.01) |
| *A61M 60/818* | (2021.01) |
| *A61M 60/822* | (2021.01) |
| *A61M 60/825* | (2021.01) |

(52) U.S. Cl.
CPC ........ *A61M 60/237* (2021.01); *A61M 60/242* (2021.01); *A61M 60/508* (2021.01); *A61M 60/814* (2021.01); *A61M 60/818* (2021.01); *A61M 60/822* (2021.01); *A61M 60/825* (2021.01); *A61M 2205/3606* (2013.01); *A61M 2205/3633* (2013.01)

(58) Field of Classification Search
CPC .............. A61M 60/508; A61M 60/814; A61M 60/818; A61M 60/822; A61M 60/825; A61M 2205/3606; A61M 2205/3633
See application file for complete search history.

(56) References Cited

U.S. PATENT DOCUMENTS

| | | | | |
|---|---|---|---|---|
| 5,853,409 A | * | 12/1998 | Swanson ................ | A61B 18/00 |
| | | | | 600/374 |
| 6,116,862 A | | 9/2000 | Rau et al. | |
| 7,425,119 B2 | * | 9/2008 | Bolz ....................... | F02B 33/40 |
| | | | | 123/565 |
| 10,857,275 B2 | | 12/2020 | Granegger | |
| 2001/0053330 A1 | | 12/2001 | Ozaki | |
| 2005/0261543 A1 | | 11/2005 | Abe et al. | |
| 2006/0057006 A1 | * | 3/2006 | Williams ............ | F04D 13/0633 |
| | | | | 417/423.1 |
| 2006/0081226 A1 | * | 4/2006 | Bolz ................... | F04D 25/0606 |
| | | | | 123/565 |
| 2014/0303426 A1 | * | 10/2014 | Kerkhoffs ........... | A61M 60/216 |
| | | | | 600/16 |
| 2015/0174311 A1 | * | 6/2015 | McLevish ........... | B21D 53/027 |
| | | | | 422/46 |
| 2016/0213827 A1 | * | 7/2016 | Tanner ................ | A61M 60/422 |
| 2018/0289877 A1 | * | 10/2018 | Schumacher ....... | A61M 60/148 |
| 2018/0326133 A1 | * | 11/2018 | Hansen ............... | A61M 60/148 |
| 2021/0239121 A1 | * | 8/2021 | Helmis .............. | F04D 29/5806 |

FOREIGN PATENT DOCUMENTS

| | | | | |
|---|---|---|---|---|
| WO | WO 1997/049439 A1 | 12/1997 | | |
| WO | WO 1998/011347 A1 | 3/1998 | | |
| WO | WO-9949912 A1 | * | 10/1999 | .......... H02K 5/1285 |
| WO | WO 2018/209130 A1 | 11/2018 | | |

OTHER PUBLICATIONS

International Search Report for Application No. PCT/EP2020/054949, dated May 4, 2020, European Patent Office, Rijswijk, Netherlands, pp. 1-6.

First Office Action and Search Report issued for Chinese Application No. 202080016385.4 dated Apr. 2, 2024 (with English translation) (18 pp.).

* cited by examiner

IMPLANTABLE BLOOD PUMP FOR ASSISTING A HEART FUNCTION

CROSS-REFERENCE TO RELATED APPLICATIONS

This application is a 371 nationalization of international patent application PCT/EP2020/054949 filed Feb. 25, 2020, which claims priority under 35 USC § 119 to European patent application EP 19159286.4 filed Feb. 26, 2019. The entire contents of each of the above-identified applications are hereby incorporated by reference.

TECHNICAL FIELD

The present application lies in the field of medical technology and in particular in the field of implantable blood pumps for assisting a heart function. The application relates to an implantable blood pump for assisting a heart function.

BRIEF DESCRIPTION OF THE DRAWINGS

There are shown.

DETAILED DESCRIPTION

Figure 1:
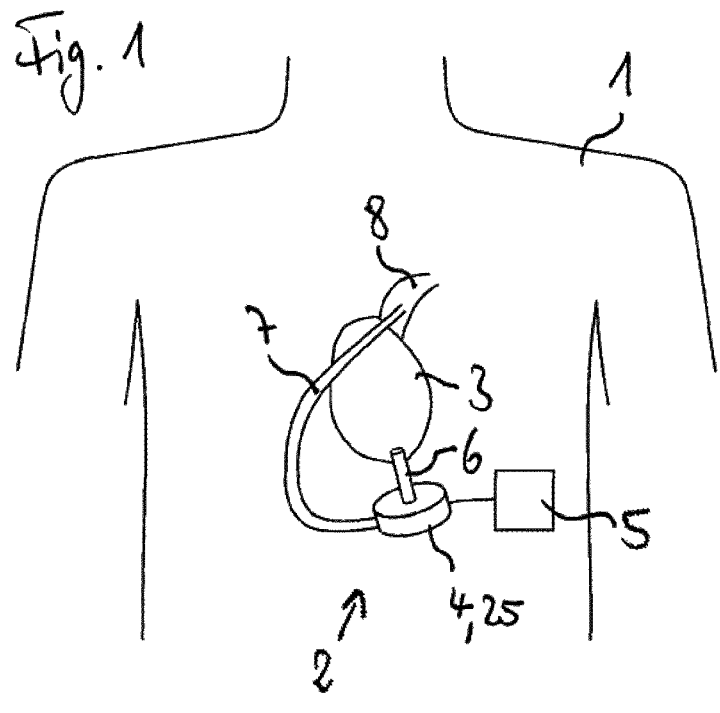
FIG. 1 a schematic view of a blood pump which is implanted in a patient's body, FIG. 2 a further schematic view of the blood pump, FIG. 3 a schematic detailed view of the blood pump, FIG. 4 a further schematic view of the blood pump, FIG. 5 a schematic view of a heat distributor, FIG. 6 an illustration of a heat flow in the blood pump FIG. 7 a view of a blood pump according to a further embodiment, FIG. 8(*a*) a view of a blood pump according to a further embodiment and FIG. 8(*b*) a schematic cross-sectional view of the blood pump.

Blood pumps, in particular heart pumps, are known from the state of the art. These blood pumps can be used if a patient's heart function must be assisted or replaced. Current systems which are hereby used are so-called VAD (ventricular assist devices). Such blood pumps can be designed for example as so-called LVAD (left ventricular assist device), RVAD (right ventricular assist device) or BiVAD (bi-ventricular assist device). In addition to the blood pump which, in operation, is implanted in the patient, these systems generally comprise a control device which is disposed for example outside a patient's body and connected to the blood pump via a line (driveline). The blood pump generally comprises a motor with a stator and with a rotor, which is provided with a blading and is arranged in a flow channel of the blood pump. The motor of the blood pump can be actuated by energy delivered by the control device, by for example a current flow being produced in windings of the stator, by means of which the rotor is set in rotation together with the blading for conveying the blood of the patient. For example, reference is made to the state of the art of publication EP 3 181 163 A1.

Since fully implantable VADs are generally actuated by a likewise implanted electric motor, the heat management plays an important role in the development of these heart pumps. Energy dissipation of the motor should be removed entirely via the blood stream. Blood-guiding components should thereby heat up by no more than two Kelvin. In order to maintain these specifications, for example as efficient a motor as possible can be used and/or the hydraulic efficiency can be optimised. In order to improve the efficiency of the motor, for example more space can be reserved for the coils or magnetisable iron, which however leads to a greater spatial requirement of the VAD.

It is one object of the present application to propose an improved implantable blood pump for assisting a heart function. In particular, the proposed blood pump is intended to reduce blood damage as a result of heat produced by the blood pump. In addition, the proposed blood pump is intended to be operable at high powers and reducible in size without blood damage occurring because of the heat produced by the blood pump.

The proposed implantable blood pump, in particular heart pump, is suitable for assisting a heart function. The blood pump comprises a heat source and a wall which delimits a flow channel. In addition, the blood pump comprises a heat distributor for distributing heat produced by the heat source to a surface of the wall. In order to transfer heat from the heat source to the blood conveyed in the flow channel, the heat distributor is connected thermally conductively to the heat source and thermally conductively to a side of the wall orientated away from the flow channel.

By means of the heat distributor, heat can be transferred from the heat source to the wall which delimits the flow channel and can be transferred to the blood conveyed by the flow channel. A spatial distribution of the heat to an enlarged surface area of the wall is hereby achieved and an effective cooling surface area is enlarged. Hence the blood is heated to less high temperatures so that a thermal load or blood damage by the heat distributor can be avoided. As a result, smaller blood pumps are possible which can be operated at greater power and with lower volume flows.

Typically, the heat distributor is not disposed completely in a region of the blood pump which is situated directly between the heat source and the flow channel. The heat distributor can be disposed at least partially in a region which is not covered by the heat source in a direction orientated away from the flow channel. This can be provided in order to enlarge the effective cooling surface area. It can be provided that the heat distributor has a surface orientated towards the flow channel, which is greater than a surface of the heat source orientated towards the flow channel. For example, it can be provided that the effective cooling surface area is enlarged in this way by at least 1.5 times, in particular by at least 2 times. In this way, the effective cooling surface area can be enlarged particularly efficiently. A particularly compact arrangement in radial direction can be achieved for example by the heat distributor being disposed completely in a region which is not covered by the heat source in the radial direction, i.e. in the direction orientated away from the flow channel. It can be provided for example that the heat distributor is disposed essentially or completely in a region which is situated, relative to the heat source, upstream and/or downstream.

In typical embodiments, the heat distributor has, on a side which is orientated towards the side of the wall orientated away from the flow channel, an area of at least 50 mm², in particular at least 100 mm². Heat from the heat distributor can be transferred to the wall via this surface. In this way, a particularly efficient discharge of the heat into the blood conveyed in the flow channel is achieved without a temperature of the blood being increased all too greatly locally. In some embodiments, the heat distributor is configured in essentially planar form. A thickness of the heat distributor can be for example at least 0.05 mm and/or at most 3 mm, in particular at most 1 mm. On the side which is orientated towards the side of the wall oriented away from the flow channel, the heat distributor typically has an area of at most 100 cm².

In addition, it is provided in some embodiments that the heat distributor has a heat conductivity which is greater than a heat conductivity of the wall. In this way, it is achieved that heat transferred from the heat source to the heat distributor is distributed on the heat distributor and is discharged to the blood extensively via the wall. A side of the wall orientated towards the flow channel typically has a biocompatible material, in particular titanium or a titanium alloy.

It can be provided for example that the heat distributor comprises a material with a heat conductivity of at least 25 W/(m K), at least 50 W/(m K) or at least 100 W/(m K). For example, the heat distributor can comprise a metal, in particular aluminium or copper. In order to ensure a reliable distribution of the heat on the heat distributor, the heat distributor can be configured in one piece. In typical embodiments, the heat distributor is not configured in one piece with the wall and/or with the heat source. In some embodiments, the heat distributor comprises, for an efficient heat distribution, a heat pipe or a heat tube. In addition, it is provided in general that the heat distributor is non-magnetic. The heat distributor does not typically form a component of the stator and in particular is not a winding or a magnetic core of the stator.

In typical embodiments, the implantable blood pump has an implantable pump housing. An outer wall of the housing is formed typically by a biocompatible material, in particular titanium or a titanium alloy. In addition, the blood pump has in general a motor. The motor typically comprises a stator, for example comprising windings, and a rotor, for example comprising a permanent magnet. The motor is typically received at least partially, in particular completely, in the pump housing. In addition, the pump housing surrounds and/or defines the flow channel. The rotor is typically disposed in the flow channel. In general, the rotor is likewise disposed in the flow channel. The pump housing has in general an inlet disposed upstream of the rotor and an outlet disposed downstream of the rotor. The inlet can comprise an inlet cannula. Typically, the rotor has a blading. Rotation of the rotor is in general actuatable by producing a current flow in the windings in order to convey blood. It can be provided that the heat source is received in the pump housing. In addition, it can be provided that the heat distributor is received in the pump housing. The wall can be an inner wall of the pump housing.

It can be provided in further embodiments that the wall is an outer wall of the rotor. In this case, the heat distributor is typically likewise received in the rotor. In this way, the heat can be transferred via the rotor to the blood in the flow channel.

It can be provided that the heat distributor is disposed such that the latter is fitted to transfer the heat of the heat source to a region of a main blood flow in the flow channel. The region of the main blood flow in the flow channel corresponds typically to the region of the flow channel which, during operation of the blood pump, has a flow path with the greatest volume flow. In general, the heat distributor there is disposed behind the wall and is in thermal contact with the latter wherever the main blood flow abuts against the wall in the flow channel. In this way, the heat can be transferred to regions which ensure a reliable heat discharge by the presence of the main blood flow.

It can be provided that the heat source is a motor part of the motor. In particular, it can be provided that the heat source is a stator of the motor. The heat source can in addition be a winding of the stator. However, it can also be provided that the heat source is a coil core, in particular an iron core, of the stator. In other embodiments, the heat source is a bearing part for supporting the rotor. For example, the heat source can be an active magnetic bearing for supporting the rotor or a sliding bearing for supporting the rotor. In other embodiments, the heat source is an electronic control unit for controlling the blood pump or for reading-out sensors.

In some embodiments, it can also be provided that the heat distributor is disposed such that the latter is fitted to keep the heat away from critical points in the flow channel. It can be provided for example that the heat distributor is disposed such that this is fitted to maintain the heat away from at least one stagnation point and/or from at least one recirculation point. A stagnation point corresponds to a region of the flow channel in which a volume flow, during operation, is reduced relative to the adjacent regions or comes to a standstill entirely. A recirculation point corresponds to a region of the flow channel in which the same blood particles flow past several times during operation, for example as a result of cyclic flows. Both stagnation points and recirculation points can be detected by a person skilled in the art by means of current considerations, even when the blood pump is not operating, on the basis of the structural properties of the blood pump. In the described manner, it is hence achieved that blood is not heated too greatly at the stagnation- and recirculation points. In typical embodiments, the heat distributor is disposed such that the latter is equipped to maintain the heat away from at least one thermally sensitive point in the blood flow and/or in order to direct it around the latter.

Critical points, which the heat is to be kept away from, can, in further embodiments, be narrowing points or points of mechanical pre-tension. These regions can be regions of the flow channel in which the blood, for example by narrowings of the flow channel or by blading of a rotor exerting a mechanical force effect on the blood, is more greatly stressed mechanically than in neighbouring regions. Also these regions of the flow channel should be readily identified by a person skilled in the art by means of current considerations on the basis of the structural properties of a non-operated blood pump.

Furthermore, it can be provided that the implantable blood pump has a thermal insulator. The thermal insulator can be disposed in a region of at least one critical point, in particular at least of one stagnation point and/or at least one recirculation point. For example, the thermal insulator can be disposed in the region of the critical point, in particular merely in the region of the critical point, behind the wall. The thermal insulator can be disposed between the side of the wall, orientated away from the flow channel, and the heat distributor and/or between the side of the wall, orientated away from the flow channel, and the heat source. In this way, it can be achieved by the thermal insulator that, in the region of the critical point, a reduced heat quantity is transferred from the heat distributor to the blood. A heat conductivity of the thermal insulator is typically at most 1 W/(m K). The thermal insulator can comprise for example plastic material. For example, the thermal insulator can comprise a foil, in particular a polyimide foil. In further designs, the thermal insulator can consist of a local thickened part of the wall, for example of a titanium wall, or comprise such a thickened part. In some embodiments, it can be provided that the thermal insulator is disposed between the critical point, in particular the stagnation point and/or the recirculation point, and the heat source. In this way, the heat is transferred effectively from the heat distributor to the blood flow, this heat being kept away at the same time from the critical point.

In addition, it can be provided that the implantable blood pump has a second thermal insulator which is disposed between the heat source and an outer wall of the pump housing. In this way, it is achieved that the heat is discharged into the flow channel and not into the tissue surrounding the pump housing. As a result, it is avoided that damage to the tissue surrounding the pump housing occurs.

In typical embodiments, a spacing between the heat distributor and the heat source is at most 5 mm, in particular at most 2 mm, so that an adequate heat transmission between the heat source and the heat distributor is ensured. In particular, it can be provided that a spacing between at least one winding of the stator and the heat distributor is at most 5 mm, in particular at most 2 mm. It can also be provided, for reliable heat transfer, that a spacing between the wall and the heat distributor is at most 5 mm, in particular at most 2 mm. In addition, a thermal bridge can be provided. The heat distributor can be connected via the thermal bridge to the heat source. The thermal bridge enables improved heat transfer between the heat source and the heat distributor and hence an improved heat distribution. In typical embodiments, the heat distributor is electrically insulated from the heat source, in particular from the at least one winding. It can be provided for example that the thermal bridge is electrically insulating. For example, the thermal bridge can comprise a heat-conducting paste, a heat-conducting adhesive, a metal or a ceramic. It can also be provided that the wall is connected via a heat-conducting paste, a heat-conducting adhesive or a ceramic to the heat distributor. It can also be provided that an electrical insulator, in particular a plastic material film, is provided between the thermal bridge and the wall and/or between the heat source and the wall in order that an electrical insulation of the wall is ensured.

It can be provided that the heat distributor surrounds the inner wall of the pump housing over an angle range of at least 30 degrees, in particular at least 90 degrees, 180 degrees or 270 degrees. It can also be provided that the heat distributor surrounds the inner wall completely. In this way, a large surface area can be achieved for the heat transfer and an efficient heat transfer to the wall and the blood in the flow channel. A cross-section of the flow channel can be for example round. In such embodiments, the heat distributor is typically in the shape of an annular segment or annular. The flow channel generally has a longitudinal direction along which the flow channel extends spatially. The blood pump is generally fitted to convey the blood in the longitudinal direction at least in portions. The radial direction is generally defined as the direction perpendicular to the longitudinal direction. Typically, the heat distributor surrounds the flow channel in the radial direction, partially or completely. It is provided in general that the heat distributor is tubular at least in portions or completely. It can be provided that the heat distributor has a form which corresponds to an outer circumferential surface of a cylinder or a part thereof, at least in portions or completely.

The pump housing can in addition comprise a volute. A region of the volute can form the outlet of the pump housing. A part of the flow channel delimited by the volute can be essentially spiral. In addition, the pump housing can have a further cylindrical part of the flow channel which abuts on the part delimited by the volute. It can be provided in some embodiments that the inner wall is an inner wall of the volute. Hence by means of the heat exchanger, heat can be transferred from the heat source to the inner wall of the volute. It is hereby advantageous that, in the region of the volute, a large surface is available for a heat transfer and that the blood in the region of the volute has comparatively large volume flows. Hence, a particularly efficient heat transfer with low blood damage can be achieved in this way.

The flow channel can have a thinner portion in which, in particular in some embodiments, the rotor is received entirely or partially. The volute can form a portion of the flow channel which is connected in particular to the thinner portion and is widened in the radial direction. In one embodiment in which the heat distributor enlarges the effective cooling surface area particularly efficiently, the heat distributor surrounds the volute in the radial direction partially or completely. In these embodiments, the heat distributor is therefore generally disposed in the longitudinal direction or axially at the same height as the flow channel and/or the volute and/or disposed further outwards in the radial direction, compared to the flow channel or to the volute. For example, the heat distributor can be fitted to transfer heat from the heat source of the volute, in particular to an outer wall of the volute. It can be hereby provided that the heat source overlaps with the thinner portion of the flow channel in the longitudinal direction.

Embodiments are described subsequently on the basis of the Figures.

FIG. 1 shows schematically a patient's body 1 in which a blood pump 2 is implanted for assisting a function of the heart 3. The blood pump 2 has a motor designed typically as electric motor with a rotor which is received in a biocompatible pump housing 4 of the blood pump 2. A part of the pump housing 4 is widened and configured as volute 25. The pump housing 4 is connected to a control device 5 which can likewise be implanted, as is shown schematically. The control unit 5, in some embodiments, may be received fully or partially likewise in the implanted pump housing 4. In other embodiments, the control unit 5 is arranged outside the body. The pump housing 4 additionally comprises an inlet channel 6, which is connected to an inlet cannula of the pump housing 4 and by means of which blood may be removed from a chamber of the heart 3 and conveyed via a cannula 7 into a blood vessel 8. The control unit 5 is designed to control the motor of the blood pump 2 to pump the blood.

Figure 2:
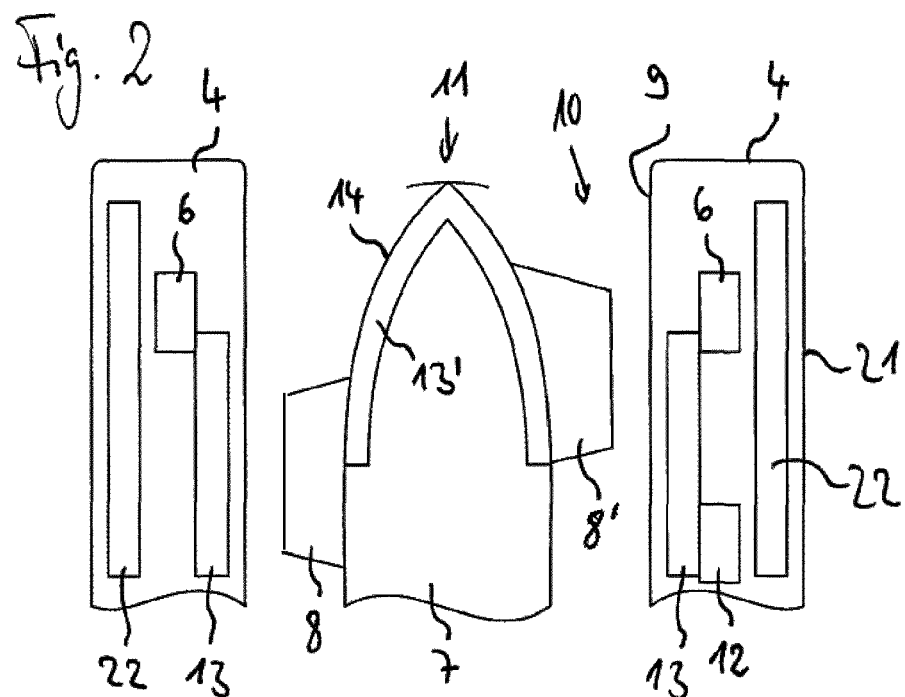

FIG. 2 shows a further schematic representation of the blood pump 2. Recurrent features in this figure and in the following figures are provided with like reference signs. The electric motor of the blood pump comprises a stator with windings 6 received in the pump housing 4. The rotor 7 of the electric motor is designed as conveying element and has a blading 8, 8'. A flow channel 10 is delimited by an essentially cylindrical inner wall 9 of the pump housing 4, in the illustrated region, through which flow channel, during operation of the blood pump 2, blood is conveyed in the direction of the cannula 7 shown in FIG. 1. In order to achieve a rotation of the rotor 7 to convey the blood, a current flow electronically controlled by the control device 5 is produced in the windings 6 of the stator. By means of the magnetic field produced by the current flow in the windings 6, an actuation magnet inside the rotor 7 and hence the entire rotor 7 can be set to rotate for conveying the blood. The rotor 7 is mounted axially and/or radially by means of a bearing part 11, illustrated merely schematically in FIG. 2, which can be designed for example as sliding-, spherical or active magnetic bearing. In addition, an electronic control unit 12, for example for reading out sensors or for controlling the blood pump, is received in the pump housing 4.

During operation of the blood pump, heat is produced by the windings 6 of the stator, by the bearing part 11 and also by the control unit 12, and is discharged to a blood flow in the flow channel 10. A heat distributor 13 is received in the pump housing 4. In addition, a further heat distributor 13' is received inside the rotor 7. The heat produced by the windings 6 of the stator, the bearing part 11 and also the control unit 12 is transferred via the heat distributors 13, 13' to the blood in the flow channel 10. A greater transition surface is hereby ensured by the heat distributors 13, 13'. The heat distributor 13 hereby transfers the heat via the inner wall 9 of the pump housing 4 to the blood. The further heat distributor 13' transfers the heat via an outer wall 14 of the rotor 7 to the blood. The outer wall 14 of the rotor 7 and the inner wall 9 of the pump housing 4, which respectively delimit the flow channel 10, are manufactured from titanium or a titanium alloy. The heat distributors 13, 13' are for example manufactured from copper and/or aluminium and therefore have greater heat conductivity than the outer wall 14 and the inner wall 9 so that the heat distributors 13, 13' effect an efficient distribution of the heat to a enlarged surface of the outer wall 14 or of the inner wall 9. A heat conductivity of the heat distributors 13, 13' can be for example 200 or 400 W/(m K).

In order that heat discharged from the above-mentioned heat sources is not discharged to a region of an outside 21 of the pump housing 4, in which the heat can be discharged only inadequately by tissue, which surrounds the pump housing 4, a thermal insulator 22 is provided between the heat sources and the outside 21 of the pump housing 4.

Figure 3:
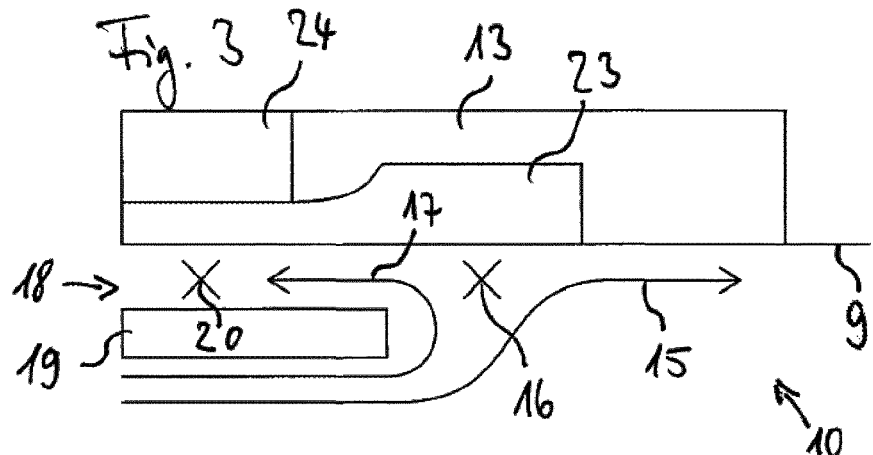

The blood flow in the flow channel 10 forms respectively, according to the structural conditions of the blood pump 2, a main blood flow 15 and also critical points, as illustrated in FIG. 3. In the region of the main blood flow 15, generally the greatest volume flows are present. Critical points in the flow channel 10 are in contrast formed by stagnation points, recirculation points, narrowing points or points of mechanical pre-tension. A cross characterised with reference number 16 represents for example a stagnation point. At this point, because of a split in the recirculation flow 17 from the main blood flow 15, a very low or, not present at all, volume flow is present so that individual blood particles staying in this region is increased. The recirculation flow 17 flows in a region of a narrowing 18 between the inner wall 9 of the pump housing 4 and an obstacle 19 in a direction opposite to the main blood flow 15. In further embodiments, the delimitation of the flow channel 10, represented by the inner wall 9 of the pump housing 4, can be formed by the outer wall 14 of the rotor 7. The obstacle 19, in some embodiments, can be formed by a part of the pump housing 4, a part connected rigidly to the pump housing 4 or by the rotor 7, in particular by the blading 8, 8' of the rotor 7. The recirculation flow 17 defines the recirculation point in the flow channel 10 which is characterised by a cross with reference number 20. The same blood particles can flow by the recirculation point 20 several times during operation. The recirculation point 20, in the example illustrated in FIG. 3, forms, at the same time, the narrowing point 20. The narrowing point 20 can be defined, for example, by a gap width between the obstacle 19 and the inner wall 9 or outer wall 14 of less than 2 mm, in particular less than 1 mm. In embodiments in which the obstacle 19 is formed by the blading 8, 8' of the rotor 7, which rotates in operation, the point with reference number 20 represents, at the same time, a point of mechanical pre-tension.

The heat distributor 13 is fitted to keep the heat to be transferred to the blood in the flow channel 10 away from the above-mentioned critical points 16, 20. It can be provided, for example, that the heat distributor 13 in regions of the main blood flow 15 abuts directly on a side of the wall 9 orientated away from the flow channel 10 whereas, in regions of the critical points 16, 20, does not abut directly on the wall 9. In the regions of the critical points 16, 20, a thermal insulator 23 is disposed between the heat distributor 13 and the wall 9 so that a heat transfer to the blood in the regions of the critical points 16, 20 is reduced. The various thermal insulators 22, 23 can be formed for example by polyimide foils. It can be provided in further embodiments that the heat distributor 13 extends such that the latter is disposed not in the regions of the critical points 16, 20 but merely in regions of the main blood flow 15 behind the wall 9 and/or is connected to the latter.

In FIG. 3, the heat source 24 is illustrated only schematically. It can hereby concern any of the various above-mentioned heat sources. The heat distributor 13 is connected thermally conductively to the heat source 24 and can abut for example directly on the latter or be distant at a spacing of less than 1 mm from the heat source 24. It can also be provided that the heat distributor 13, for production of a good heat contact, is connected via a heat-conducting paste, a heat-conducting adhesive or a ceramic to the heat source 24.

Figure 4:
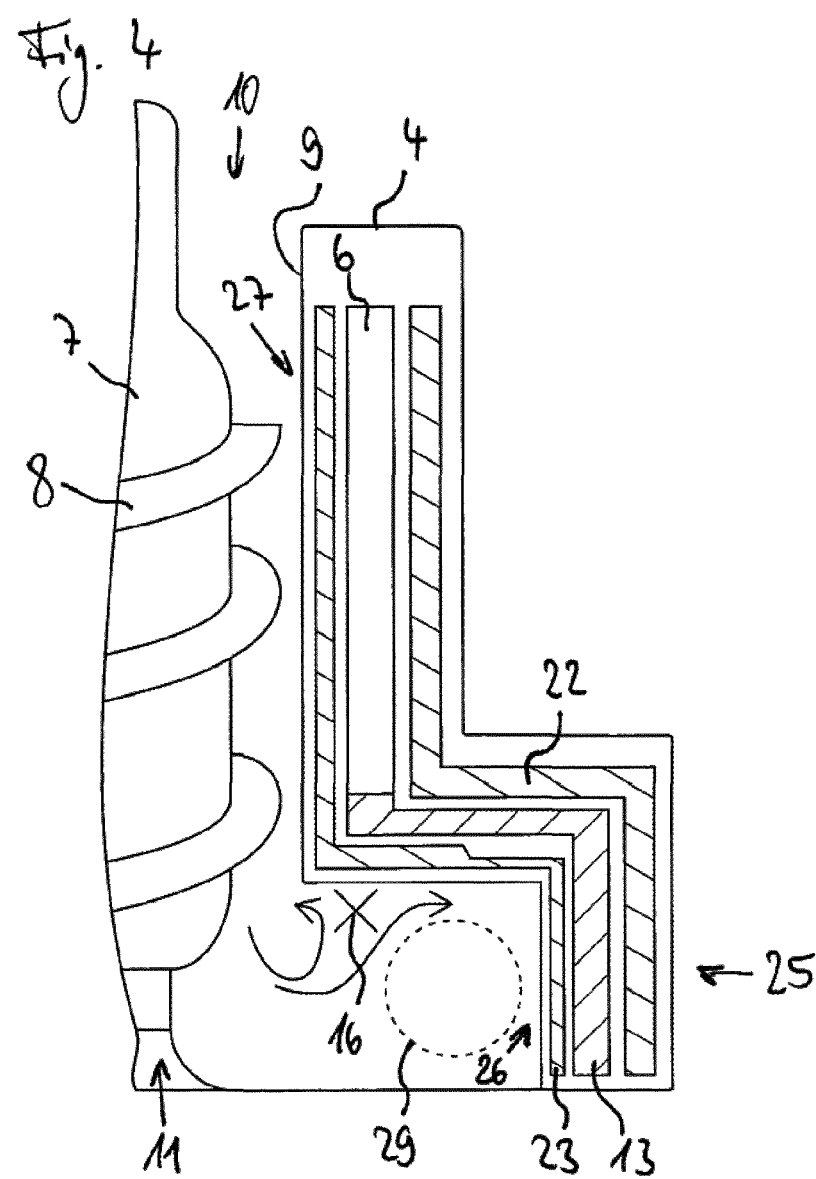

FIG. 4 shows a further schematic view of the blood pump 2. The blood pump has the volute 25 which is formed by a widened region and can be distinguished by a spiral or spiral-shaped design or spiral or spiral-shaped flow properties. In the region of the volute 25, an outlet for the conveyed blood is disposed. One position of the outlet is characterised schematically by a circle, in broken lines, with reference number 29. The heat source is formed, in the illustrated representation, by the windings 6 of the stator received in the pump housing 4. The windings 6 are disposed between the thermal insulators 22, 23. The windings 6 are connected via a thermally conductive and electrically insulating thermal bridge, for example via a ceramic, to the heat distributor 13 so that, in the region of the windings 6, heat produced by ohmic or magnetic losses, is conducted via the heat distributor 13 into the region of the volute 25. The thermal insulator 23, in the region of the volute 25, has a thinner portion 26, upstream in the region of the heat source and also, in the region of a stagnation point 16, however, a thick portion 27 so that the heat is transferred, for the large part, in the region of the volute 25 to the blood in the flow channel 10. The thermal insulators 22, 23 are in addition electrically insulating in order to ensure sufficient electrical insulation relative to the blood or to the tissue of the patient.

Figure 5:
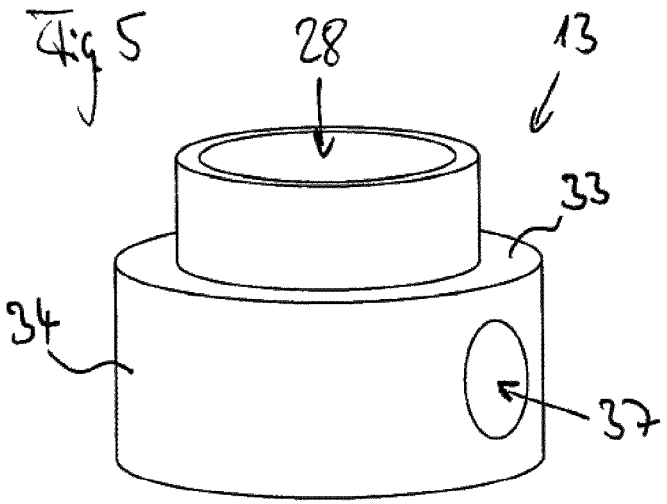

FIG. 5 shows a perspective view of the already above-described heat distributor 13. The heat distributor 13 is in fact received in the pump housing 4, however, for a better overview, the latter is not illustrated in FIG. 5. The heat distributor 13 is planar, in one-piece and annular so that the heat distributor 13 has a through-opening 28. In other embodiments, the heat distributor 13 has however the shape of an annular segment. Within the opening 28, the non-illustrated inner wall 9 of the pump housing 4, the flow channel 10 and the rotor 7 are received. In the region of the volute 25, the heat distributor 13 has a volute cover portion 34 with a diameter which is greater than in a region which is disposed in the region of the heat source. Between these regions of different diameters, a radially extending portion 33 is disposed. Hence the heat is distributed to an enlarged discharge surface by the heat distributor 13. In addition, the heat distributor 13, in the region of the outlet 29, has an opening 37 extending in radial direction. A thickness of the heat distributor 13 in radial direction can be for example 0.5 mm in the volute cover portion 34. In axial direction, the heat distributor 13 extends for example over at least a tenth, preferably over at least a sixth, of an axial extension of the pump housing 4. An inner surface of the heat distributor 13 is for example 250 mm².

Figure 6:
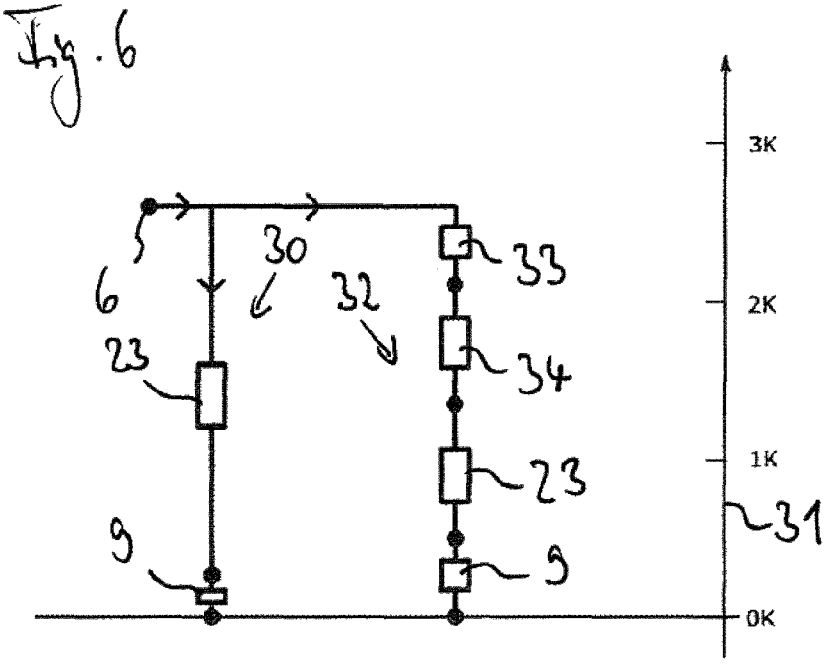

In FIG. 6, the heat flow in the blood pump 2 is shown schematically. In the region of the windings 6 of the stator, for example a heat power of 3 W is produced. This heat power is transferred, on the one hand, via a direct path 30, i.e. from the windings 6 radially inwards via the thermal insulator 23 and the inner wall 9 of the pump housing 4, to the blood in the flow channel 10. On this direct path, for example a proportion of the total heat power of less than 50% is transferred. The vertical axis 31 hereby indicates a temperature above a temperature of the blood. In addition, the heat power is transferred on a second path 32 also via the heat distributor 13 and, here in particular, its radial portion 33 and its volute cover portion 34, the thermal insulator 23 in the region of the volute 25 and also the inner wall 9 of the pump housing 2 in the region of the volute 25. On the second path 32, a greater heat power can be discharged than on the direct path 30. For example, a heat power discharged to the blood via the second path 32 can be 1.7 W.

Figure 7:
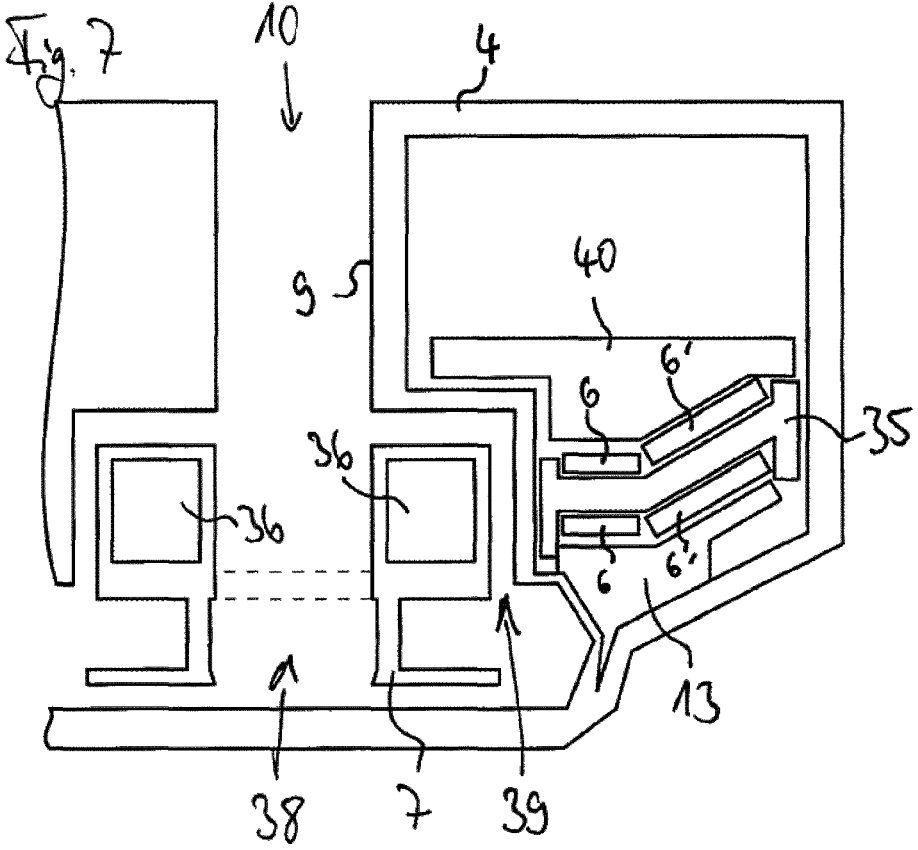

A further embodiment of a blood pump 2 is illustrated in FIG. 7. The rotor 7 of this blood pump 2 has an opening 38 which extends in axial direction and through which a main blood flow directed downwards is conveyed. In a gap 39 between the rotor 7 and the inner wall 9 of the pump housing 4 there is a recirculation flow which flows in a direction which is directed counter to the main blood flow. The rotor 7, in its interior, has a rotor magnet 36, via which a rotation of the rotor 7 can be actuated to convey blood through the stator. This stator is received in the pump housing 4 and comprises windings 6, 6' and a magnetic core 35, for example iron. In addition, an electronic unit 40 is received in the pump housing 4. During operation, both due to ohmic losses in the electronic unit 40 and in the windings 6, 6' and by remagnetisation losses in the magnetic core 35, heat is produced so that the electronic unit 40, the windings 6, 6' and the magnetic 35 core represent heat sources.

For efficient and safe discharge of the heat from the heat sources to the blood, the blood pump 2 has the heat distributor 13. The heat distributor 13 distributes the heat from the heat sources to an enlarged surface of the inner wall 9 of the pump housing 4 in the region of the volute 25. The heat distributor 13 is designed as explained above more precisely and can reduce the thermal blood loading in the gap and recirculation area 39.

Figure 8A:
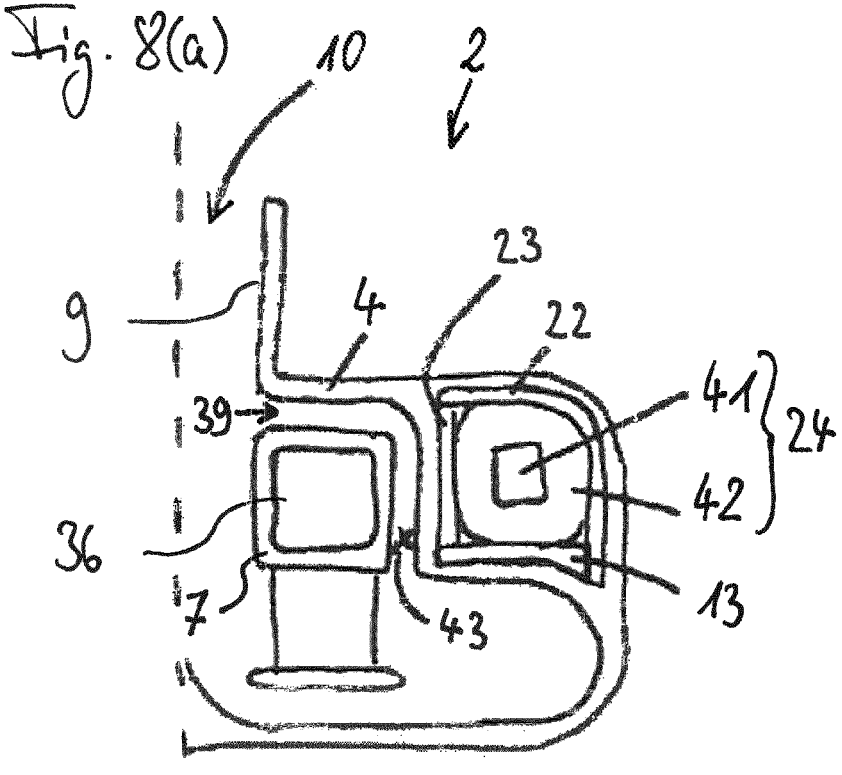
Figure 8B:
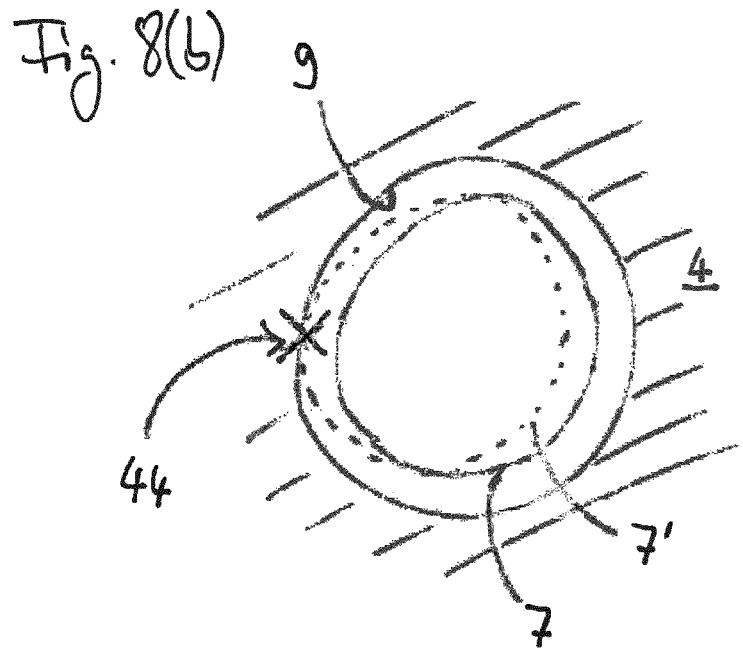

FIGS. 8(*a*) and (*b*) show schematic views of a blood pump 2 according to a further embodiment. The blood pump 2 according to this embodiment has, like the blood pump described in the context of the previous illustration, the pump housing 4 with the inner wall 9, the rotor 7 with the rotor magnet 36 being received in the flow channel 10 delimited by the inner wall 9. All the features mentioned with respect to the previous embodiments are transferable correspondingly to the blood pump 2 according to the embodiment of FIGS. 8(*a*) and (*b*). The stator forms a heat source 24 and comprises a stator core 41 and also stator windings 42 which surround the stator core 41. The heat distributor 13 is fitted and disposed to transfer heat produced by the stator windings 42 and/or the stator core 41 during operation, in the region of the volute, to the blood flow. The heat is hereby intended to be kept away from an outside of the pump housing 4, for which purpose the thermal insulator 22 is provided between the heat source 24 and the outside of the pump housing 4. In the recirculation area 39, in addition a critical point 43 is disposed, from which the heat is likewise intended to be kept away. For this purpose, the thermal insulator 23 is disposed between the stator and the recirculation area 39 so that a heat transfer to the recirculation area 39 is avoided. The heat source is hence surrounded by the thermal insulators 22, 23 and the heat distributor such that the heat is effectively transferred to the blood flow, however at the same time is kept away from the critical point 43 and the outside of the pump housing 4.

FIG. 8(*b*) shows a cross-section through the rotor 7, 7' and also the pump housing 4 with the inner wall 9. The continuous line with reference number 7 hereby shows the position of the rotor in normal operation in which the rotor 7 is received concentrically in the pump housing 4. The dotted line with reference number 7' illustrates the position of the rotor when the pump starts or is in back-up bearing operation. As is shown, the rotor 7', in this case, can be in contact with the inner wall 9 of the pump housing 4 so that the result is a critical point 44, see marking by a cross. At this critical point 44 which can be in the recirculation area 39 of the blood pump 2, it can concern a radial or axial contact point or ring. The rotor 7' abuts against the latter during the pump start and the latter also acts as back-up bearing. A pump start or a back-up bearing contact can roughen this place in the inner wall 9. As a result, this place has a tendency more and more to form deposits and should likewise not be thermally loaded. As a result of the thermal insulator 23 which, as is shown above for the critical point 43, can be disposed between the critical point 44 and the heat source 24, avoidance of increased blood damage due to thermal loading is achieved efficiently.

Features of the various embodiments disclosed only in the embodiment examples can be combined together and claimed individually.

To clarify the use of and to hereby provide notice to the public, the phrases "at least one of <A>, <B>, . . . and <N>" or "at least one of <A>, <B>, . . . or <N>" or "at least one of <A>, <B>, <N>, or combinations thereof" or "<A>, <B>, . . . and/or <N>" are defined by the Applicant in the broadest sense, superseding any other implied definitions hereinbefore or hereinafter unless expressly asserted by the Applicant to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed. Unless otherwise indicated or the context suggests otherwise, as used herein, "a" or "an" means "at least one" or "one or more."

The present application concerns in particular the following aspects:

1. Implantable blood pump (2) for assisting a heart function, comprising a heat source (24) and a wall (9, 14) which delimits a flow channel (10), characterised by a heat distributor (13) for distributing heat produced by the heat source (24) to a surface of the wall (9, 14), the heat distributor (13), for transferring heat from the heat source (24) to blood conveyed in the flow channel (10), being connected thermally conductively to the heat source (24) and thermally conductively to a side of the wall (9, 14) orientated away from the flow channel (10).

2. Implantable blood pump (2) according to aspect 1, characterised in that the heat distributor (13), on a side which is orientated towards the side of the wall (9, 14), orientated away from the flow channel (10), has a surface area of at least 50 mm².

3. Implantable blood pump (2) according to one of the aspects 1 or 2, characterised in that the heat distributor (13) has a heat conductivity which is greater than a heat conductivity of the wall (9, 14).

4. Implantable blood pump (2) according to one of the aspects 1 to 3, characterised in that the heat distributor (13) comprises a material with a heat conductivity of at least 50 W/(m K) or at least 100 W/(m K).

5. Implantable blood pump (2) according to one of the aspects 1 to 4, characterised in that the heat distributor (13) is disposed such that the latter is fitted to transfer the heat of the heat source (24) to a region of a main blood flow (15) in the flow channel (10).

6. Implantable blood pump (2) according to one of the aspects 1 to 5, characterised in that the heat distributor (13) is disposed such that the latter is fitted to keep the heat away from at least one stagnation point (16) and/or from at least one recirculation point (20).

7. Implantable blood pump (2) according to one of the aspects 1 to 6, characterised by a thermal insulator which is disposed in a region of at least one stagnation point (16) and/or of at least one recirculation point (20) between the side of the wall (9, 14), orientated away from the flow channel (10), and the heat distributor (13).

8. Implantable blood pump (2) according to one of the aspects 1 to 7, characterised in that the heat distributor (13) is connected via a thermal bridge, which comprises in particular a heat-conducting paste, a heat-conducting adhesive, a metal or a ceramic, to the heat source (24).

9. Implantable blood pump (2) according to one of the aspects 1 to 8, characterised by an implantable pump housing (4), the wall being an inner wall (9) of the pump housing (4).

10. Implantable blood pump (2) according to aspect 9, characterised in that the heat distributor (13) surrounds the inner wall (9) of the pump housing (4) over an angle range of at least 30 degrees, in particular at least 90 degrees.

11. Implantable blood pump (2) according to one of the aspects 1 to 10, characterised by a motor, the heat source (24) being a motor part of the motor.

12. Implantable blood pump (2) according to aspect 11, characterised in that the motor part is a stator of the motor.

13. Implantable blood pump (2) according to one of the aspects 1 to 12, characterised by a rotor (7), the heat source (24) being a bearing part (11) for supporting the rotor (7).

14. Implantable blood pump (2) according to aspect 13, the wall being an outer wall (14) of the rotor (7).

15. Implantable blood pump (2) according to one of the aspects 9 to 14, characterised in that the pump housing (4) comprises a volute (25), the inner wall (9) being an inner wall of the volute (25).

The invention claimed is:

1. Implantable blood pump for assisting a heart function, comprising:

an implantable pump housing;

a heat source and a wall which delimits a flow channel;

a heat distributor for distributing heat produced by the heat source to a surface of the wall, the heat distributor, for transferring heat from the heat source to blood conveyed in the flow channel, being connected thermally conductively to the heat source and thermally conductively to a side of the wall orientated away from the flow channel;

wherein the wall is an inner wall of the pump housing, the pump housing comprises a volute, and the inner wall of the pump housing is an inner wall of the volute;

wherein the heat source is a stator of a motor, the stator comprising a stator core; and wherein the heat distributor is configured to transfer heat from the stator to the inner wall of the volute.

2. The implantable blood pump of claim 1 wherein the heat distributor is disposed such that the latter is fitted to keep the heat away from at least one stagnation point and/or from at least one recirculation point.

3. The implantable blood pump of claim 1 wherein the heat distributor is disposed such that the latter is fitted to keep the heat away from at least one narrowing point and/or from a point of mechanical pre-tension.

4. The implantable blood pump of claim 1 wherein a thermal insulator which is disposed in a region of at least one critical point, the at least one critical point comprising at least one stagnation point and/or at least one recirculation point, between the side of the wall, orientated away from the flow channel, and the heat distributor, and/or between the side of the wall, orientated away from the flow channel, and the heat source.

5. The implantable blood pump of claim 4 wherein the thermal insulator is disposed between the at least one critical point and the heat source.

6. The implantable blood pump of claim 4 wherein the thermal insulator has a heat conductivity of at most 1 W/(m K).

7. The implantable blood pump of claim 4 wherein the thermal insulator comprises a polyimide foil.

8. The implantable blood pump of claim 4 wherein the thermal insulator consists of a local thickened part of the wall.

9. The implantable blood pump of claim 8, wherein the wall comprises a titanium wall.

10. The implantable blood pump of claim 1 wherein the heat distributor is disposed at least partially in a region which is not covered by the heat source in a direction orientated away from the flow channel, such that an effective cooling surface area is enlarged.

11. The implantable blood pump of claim 1 wherein the heat distributor surrounds the flow channel in a radial direction, partially or completely.

12. The implantable blood pump of claim 1 wherein the heat distributor surrounds the inner wall of the pump housing over an angle range of at least 90 degrees.

13. The implantable blood pump of claim 1 wherein the heat distributor has a form which corresponds to an outer circumferential surface of a cylinder or a part thereof, at least in portions or completely.

14. The implantable blood pump of claim 1 comprising a rotor, the heat source being a bearing part for supporting the rotor.

15. The implantable blood pump of claim 14 wherein the heat distributor is received in the rotor.

16. The implantable blood pump of claim 14 further comprising the wall being an outer wall of the rotor.

17. The implantable blood pump of claim 1 wherein the heat distributor surrounds the volute in a radial direction partially or completely.

18. The implantable blood pump of claim 1 wherein the heat distributor is fitted to transfer heat from the heat source to an outer wall of the volute.

19. The implantable blood pump of claim 1 wherein the heat distributor has, on a side which is orientated towards the side of the wall orientated away from the flow channel, an area of at least 50 mm².

20. The implantable blood pump of claim 1 wherein the heat distributor surrounds the inner wall of the pump housing over an angle range of at least 30 degrees.

* * * * *